United States Patent [19]

Edwards

[11] 4,116,646
[45] Sep. 26, 1978

[54] FILTER UNIT

[75] Inventor: James H. Edwards, Winchester, Mass.

[73] Assignee: Millipore Corporation, Bedford, Mass.

[21] Appl. No.: 798,934

[22] Filed: May 20, 1977

[51] Int. Cl.$^2$ .................. B01D 19/00; A61M 5/16
[52] U.S. Cl. .................. 55/159; 128/214 R; 210/94; 210/436; 210/DIG. 23
[58] Field of Search ............ 55/159; 128/2 F, 214 R, 128/214 C, 214.2; 210/94, 436, 441, 446, 448, 490, DIG. 23

[56] References Cited

U.S. PATENT DOCUMENTS

| | | | |
|---|---|---|---|
| 3,003,500 | 10/1961 | Barton et al. | 210/94 X |
| 3,316,908 | 5/1967 | Burke | 210/94 X |
| 3,523,408 | 8/1970 | Rosenberg | 55/159 |
| 3,631,654 | 1/1972 | Riely et al. | 55/159 |
| 3,650,093 | 3/1972 | Rosenberg | 55/159 |
| 3,803,810 | 4/1974 | Rosenberg | 55/159 |
| 3,854,907 | 12/1974 | Rising | 55/159 |
| 4,004,587 | 1/1977 | Jess | 55/159 X |
| 4,013,072 | 3/1977 | Jess | 210/94 X |
| 4,031,891 | 6/1977 | Jess | 210/436 X |

Primary Examiner—Charles N. Hart
Assistant Examiner—Robert H. Spitzer
Attorney, Agent, or Firm—Irons and Sears

[57] ABSTRACT

The arrangement of the disclosure comprises a filter unit having an upper, inlet chamber and a lower, outlet chamber. A hydrophilic filter separates the upper chamber from the lower chamber and a lower placed hydrophobic filter or membrane separates the lower chamber and the upper chamber. A liquid reservoir is provided in the first chamber between the filter and membrane, and a gas reservoir is provided in the second chamber between the filter and membrane.

A liquid admitted to the upper, inlet chamber with a forward differential pressure, that is with the pressure in the upper chamber larger than that in the lower chamber, will flow through the upper hydrophilic filter into the lower chamber. If any gas accumulates it cannot accumulate above the level of the lower hydrophobic membrane. Accordingly no gas flows out of the lower, outlet chamber in the forward direction. If there is a reverse differential pressure, reverse liquid flow is prevented by the hydrophobic membrane and by air trapped above the lower hydrophobic filter against the upper, wet hydrophilic filter. If liquid supply to the upper chamber fails and a forward pressure differential exists between the chambers, forward gas flow is prevented by the wet upper hydrophilic filter and the liquid trapped above the hydrophobic filter. Therefore the unit filters the liquid flow, vents gas in the outlet chamber to the inlet chamber, prevents forward gas flow, and prevents reverse liquid flow.

21 Claims, 6 Drawing Figures

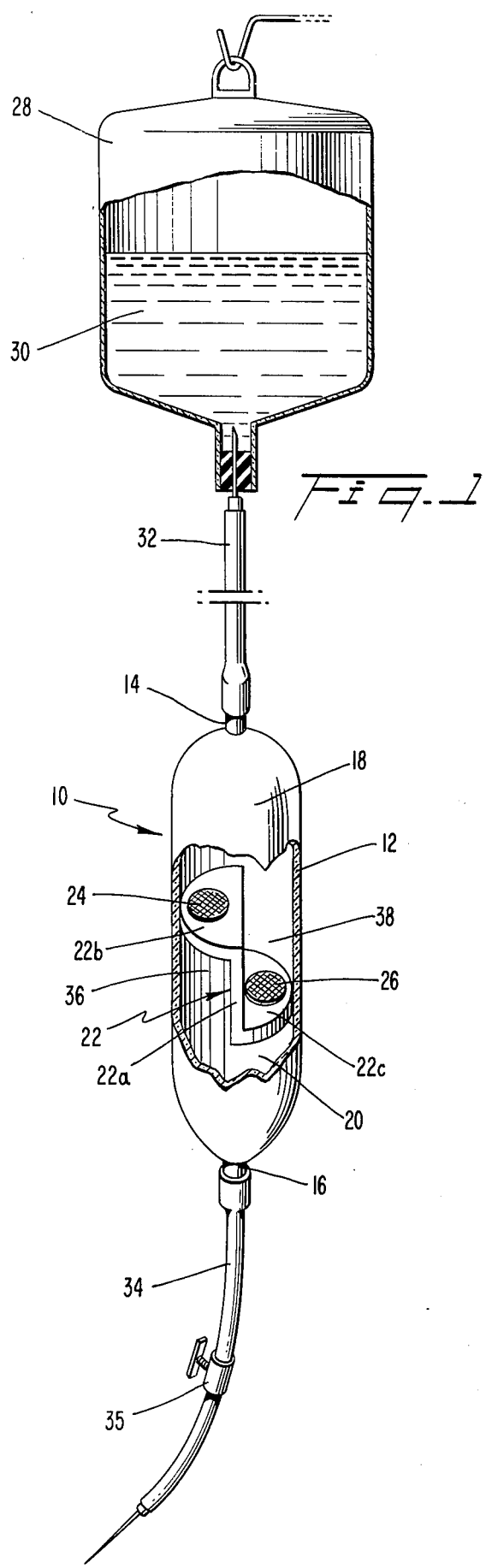
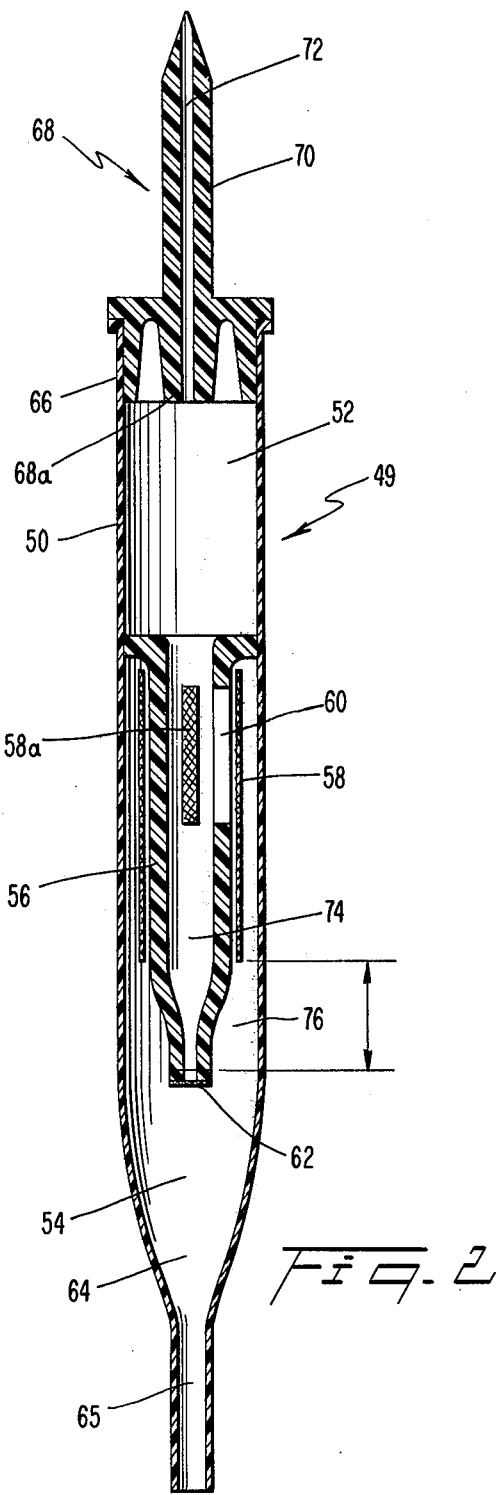

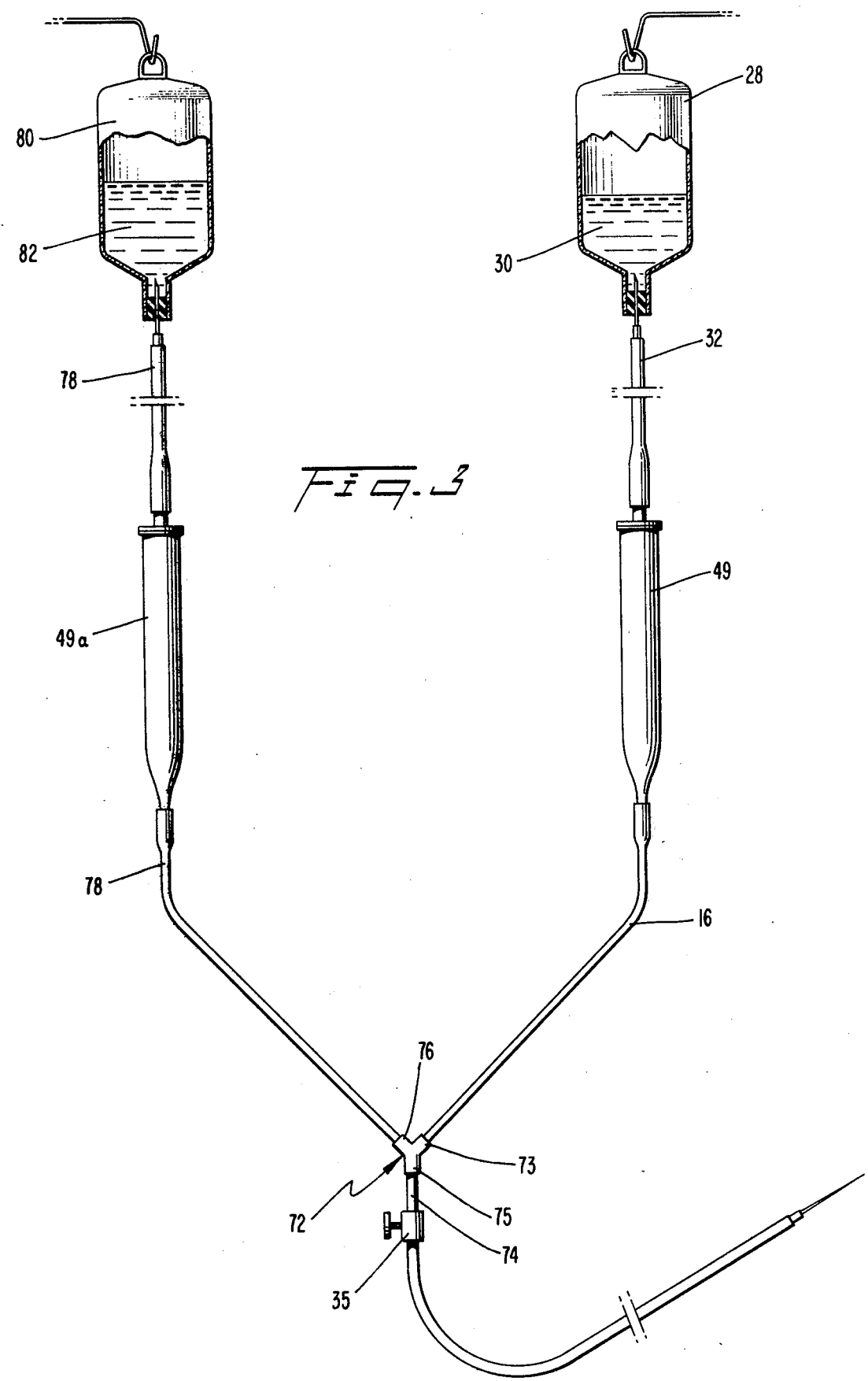

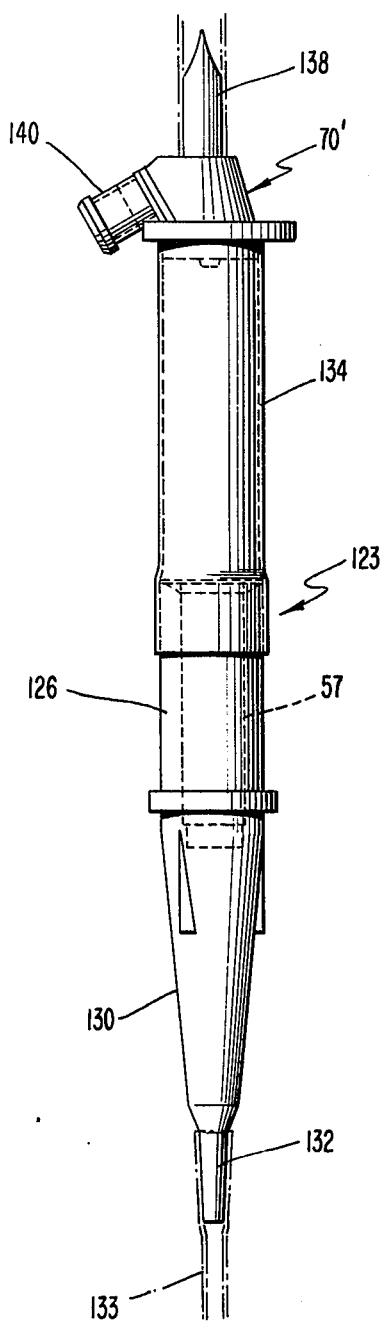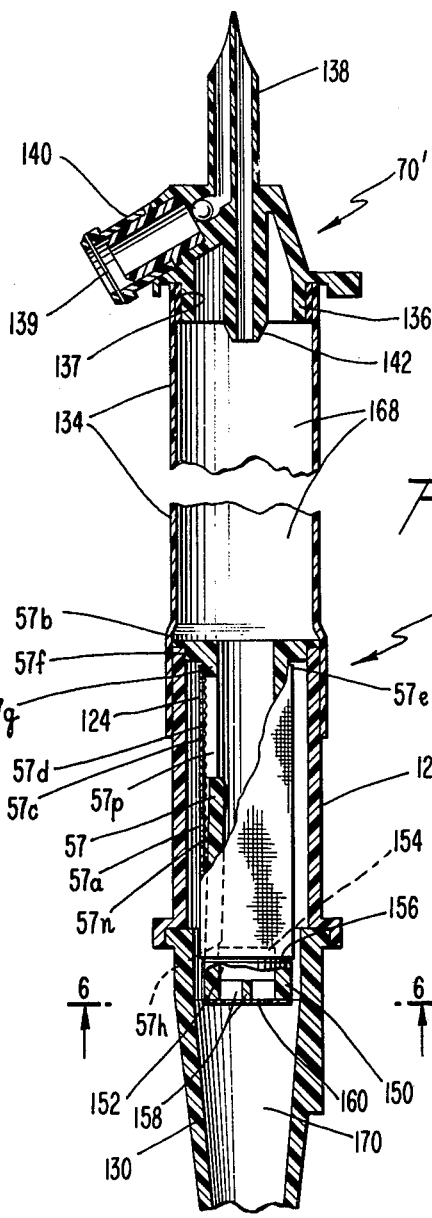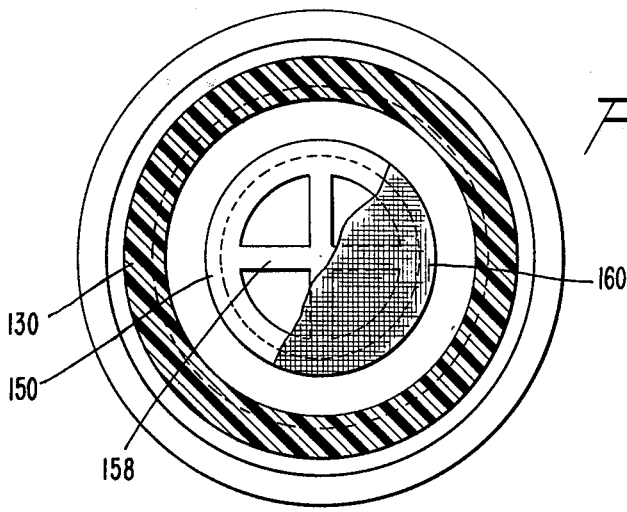

FILTER UNIT

BACKGROUND OF THE INVENTION

It is known to use in a single filter holder or unit both a hydrophobic and a hydrophilic filter. For example, a hydrophilic filter may be used to filter fluid passing through a chamber in the pathway from an intravenous set for example to a patient. The filter holder may also hold a hydrophobic filter to vent gas accumulated in the holder. It is also known to employ a hydrophilic membrane or filter to filter a primary solution and a hydrophobic membrane disposed in the air vent whereby the hydrophilic filter may function as a valve to prevent the admission of air when the supply of the primary solution is exhausted. Various valving means have been proposed to prevent the reverse flow of a fluid being administered to a patient. In some instances filters have been employed to function as cut-off valves. As representative of these various proposals the following patents may be cited: British Patent 538,728/41 issued Aug. 14, 1941; U.S. Pat. No. 2,770,234 to Nesset et al, Apr. 5, 1954; U.S. Pat. No. 3,506,130 to Shaye, Apr. 14, 1970; U.S. Pat. No. 3,886,937 to Bobo et al, June 3, 1975; U.S. Pat. No. 3,967,620 to Noiles, July 6, 1976; U.S. Pat. No. 3,993,066 to Virag, Nov. 23, 1976; and U.S. Pat. No. 4,013,072 to Jess.

In some of these patents a forward flow is cut off by the filter if there should be failure to supply solution. Various filter combinations are also shown providing the application of a so-called "piggyback" arrangement for administering a medicament or other solution preferentially during the administration of a parenteral supply.

SUMMARY OF THE INVENTION

According to the present arrangement, a filter unit has, when oriented as in operation, an upper chamber and a lower chamber, a hydrophilic filter separating the chambers and a lower hydrophobic membrane separating the chambers. Parenteral fluid, for example, may be administered in the usual manner from a container through a conduit into the upper or inlet chamber from whence it flows through the hydrophilic filter into the lower chamber. As the fluid flows on down leaving the lower outlet chamber, any gas that accumulates below the hydrophobic membrane is vented through the lower hydrophobic membrane. Some liquid will remain in a liquid reservoir in the upper chamber below the hydrophilic filter, and some gas will accumulate in the lower chamber in a gas reservoir above the hydrophobic membrane. Should liquid supply to the inlet chamber fail, and the weight of the fluid in the lower conduit leading from the lower chamber cause a differential pressure in the forward direction between the chambers, forward gas flow will be prevented by the wetted hydrophilic filter and the liquid trapped in the liquid reservoir above the hydrophobic membrane. If there should be a reverse differential pressure, for example as may exist in a so-called piggyback arrangement when it is desired to supply a solution in preference to the parenteral solution, the reverse pressure differential does not cause a reverse liquid flow. In such a case reverse flow is prevented by the liquid against the hydrophobic membrane and the gas trapped in the gas reservoir below the hydrophilic filter. Accordingly the desired preferential flow of solution is attained and does not result in a reverse flow into the primary parenteral solution.

BRIEF DESCRIPTION OF THE DRAWINGS

The various advantages, objects, and novel features of the invention will be more fully apparent from the following detailed description when read in connection with the accompanying drawings in which:

FIG. 1 is a perspective view partially broken away of one embodiment of the invention in simplified form to illustrate the principles of operation, FIG. 4 is a face view of another embodiment of the invention;

FIG. 5 is a longitudinal cross-sectional view in a vertical plane of the embodiment of FIG. 4; and FIG. 6 is an enlarged cross-sectional view along the lines 6—6 of FIG. 5.

DETAILED DESCRIPTION

Figure 2:
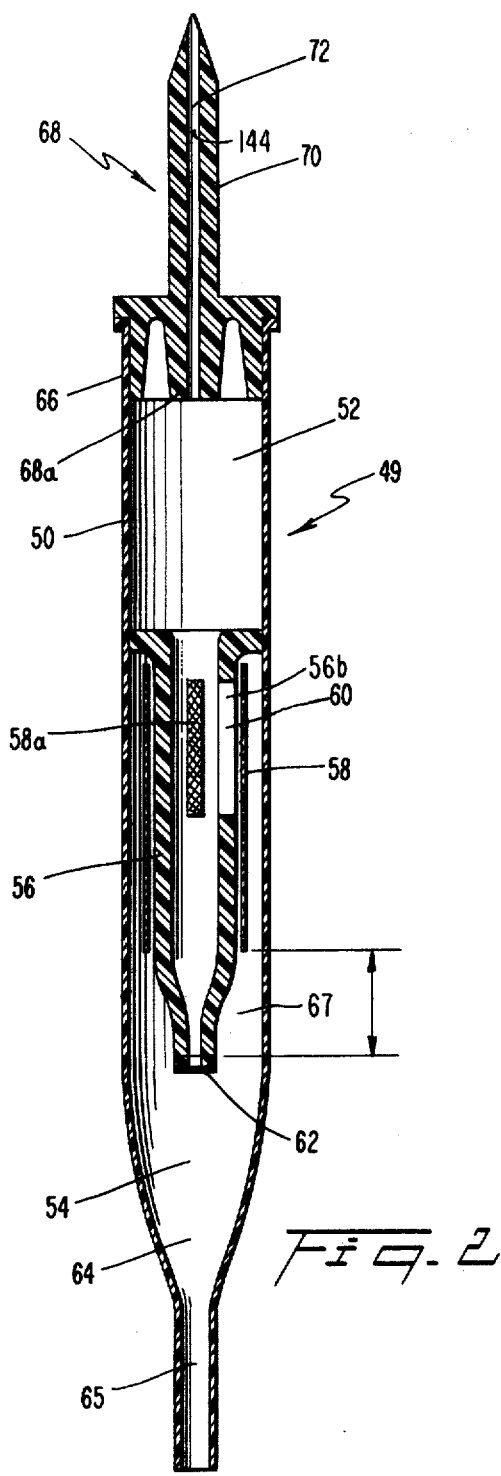
FIG. 2 is a cross-sectional view in a vertical axial plane of another embodiment of the invention.

Referring now to FIG. 1, a filter unit 10 has walls 12 which are preferably resilient. In this embodiment the walls 12 are generally cylindrical in shape, tapered slightly on the upper end 14 to receive tubing 32, which may be in sealed relationship simply by virtue of the tight, stretch fit of the tubing, and tapered at the lower end to a narrowed exit port 16. The filter holder 10 is divided internally into two compartments or chambers, these being an upper chamber 18 and a lower chamber 20, by a dividing wall extending to and sealed to the outer walls 12. The dividing wall 22 comprises a vertical, rectangular portion 22a sealed at its vertical sides to walls 12; an upper semicircular shaped portion 22b and a lower semicircular shaped portion 22c. The circular edges of the semicircular shaped portions 22b and 22c are sealed to the walls 12. In the upper horizontal wall portion 22 is fitted in sealed relationship by any suitable means a hydrophilic microporous filter 24, and in the lower horizontal wall portion 22c is fitted in sealed relationship by any suitable means a hydrophobic microporous membrane 26. The various seals may be accomplished by any suitable means. If desired, supports (not shown) for the filters 24 and 26 may be provided. A container 28 of parenteral solution 30 may be suspended in the usual manner above the filter unit 10 or the flexible tubing 32 leading therefrom to the inlet 14 with which it is connected in the usual liquid-tight manner. A lower flexible passageway of tubing 34 is sealed to the exit port 16.

In operation, the container 28 is hung in the usual manner with a substantially vertical axis and "spiked" to provide fluid communication to the upper flexible tubing 32. The axis need not be an axis of symmetry. If the liquid flow does not commence readily, the resilient walls 12 of the upper chamber 18 may be squeezed lightly to expel air and relaxed to permit the parenteral solution liquid to flow down through the upper flexible tubing to wet the hydrophilic microporous filter. Means (not shown) are provided to admit air to the container to replace the lost liquid, or container 28 may be collapsible. The resilient walls of the lower chamber 20 may now be squeezed lightly and relaxed to expel air through the hydrophobic filter 26 from the lower chamber 20 into the upper chamber 18 and induce liquid flow. The lower flexible tubing should be clamped shut at this time as by a clamp such as clamp 35 in order to force the air upward through the filter and not down through the tubing. Liquid now flows through the upper hydrophilic membrane 24 into the chamber 20 and then down to the lower flexible tubing 34 toward the patient. Squeezing of the lower chamber 20 may be continued until the lower flexible tubing 34 and the lower chamber 20 are filled with liquid up to the level of the microporous hydrophobic membrane 26. Thereafter the clamp 35 may be opened and administration of the fluid begun in the usual fashion after all air is expelled by liquid flow.

As the liquid passes into the patient from the lower flexible tubing 34 it is replaced by liquid which passes through and drips from or flows from the hydrophilic filter 24. At the same time air has collected in the lower chamber in the space 36, which we may term an air or gas reservoir, between the lower hydrophobic membrane 26 and the upper hydrophilic filter 24. Besides filtering, this arrangement performs three functions. First, any air or gas which would tend to accumulate in the lower chamber 20 from liquid which otherwise might proceed to the patient may be vented through the hydrophobic membrane 26. Second, if the liquid flow from the container 28 stops for some reason, for example by reason of the container being empty, then notwithstanding the forward pressure differential between upper chamber 18 and the lower chamber 20, air is prevented from passing through the upper chamber 18 into the lower chamber 20. The reason is that the hydrophilic filter 24, being wet, prevents the passage of air through it by reason of the bubble point of the filter. At the same time when the upper chamber 18 is emptied to the level of the hydrophilic filter 24, a reservoir of liquid remains in what we may term the liquid reservoir 38 in the upper chamber between the level of the upper hydrophilic filter 24 and the lower hydrophobic membrane 26. The liquid in the liquid reservoir space 38 cannot pass through the hydrophobic membrane by reason of the intrusion point being greater than the pressure differential. The liquid in the liquid reservoir 38 thus blocks or traps against the hydrophobic membrane the access of air in the forward direction from the upper chamber 18 to the hydrophobic membrane. Accordingly any flow of air in the forward direction from the upper chamber 18 to the lower chamber 20 is prevented.

Third, in the event of a reverse pressure differential, that is in the event the pressure in the lower chamber 20 exceeds the pressure in the upper chamber 18, a backward flow is prevented. Liquid cannot flow through the hydrophobic filter 26, because of its intrusion point. The accumulation of air in the air space or gas reservoir 36 prevents access of liquid from the lower chamber 20 to the hydrophilic filter 24. Air or gas cannot pass through filter 24 because of the bubble point, and blocks access of liquid to the first chamber. Therefore reverse liquid flow is blocked or prevented.

Among the advantages of the arrangement are that in normal operation, besides the filtering action, as will appear more fully hereafter, the air space or air reservoir 36 may itself act as a drip chamber and therefore, it is not necessary to append a separate drip chamber. Elimination of downstream entrapped air is insured by virtue of the hydrophilic filter 24 and the venting by the hydrophobic membrane 26. The operator need learn no new or unusual techniques. An arrangement such as that described provides low cost components and integrity testing of the set is relatively simple and reliable. For example filters may be tested by wetting with Freon and challenging with an air pressure below their bubble point. The embodiment just described affords a simple and readily visualizable exposition of the principles of the invention.

Referring to FIG. 2, a filter unit 49 again having preferably resilient walls 50 which may be generally cylindrical in shape with an axis vertical during operation, (the axis need not be an axis of symmetry) is divided into an upper chamber 52 and a lower chamber 54 by a vase-shaped, rigid dividing member 56. Along the upper wall of dividing member 56 is a vertically arranged microporous hydrophilic filter 58 sealed around longitudinal ribs 56b which form passageways 60 through the member 56. The hydrophilic filter 58 is wrapped around the support member and heat sealed to it on all edges. A heat seal may be effected by pressure and enough heat to melt the surface of the support member forcing the molten plastic into the pores of the filter. Sealed across the base of the dividing member 56 is a microporous hydrophobic membrane 62, which also may be heat sealed thereto. There may be more than one such membrane, one being here deemed adequate. The upper lip of the vase-shaped dividing member 56 is sealed throughout its circumference, by any suitable means to the walls 50 of the holder.

Membrane supports (not shown) may be provided on both upstream and downstream sides of the hydrophilic filter 58. Nevertheless I provide a membrane support on the upstream side only, because pressure tending to rupture the rather fragile filter 58 is not likely to be exerted in the downstream direction, relief being afforded by the return of air or liquid to the container above. However, when the lower chamber 54 is compressed, in a manner to be described, a substantial pressure may be exerted against the hydrophilic fiter 58 in the upstream direction. Therefore support on the upstream side of the filter is desirable. Any released gas will be vented through the hydrophobic membrane 62 or added to the gas reservoir 67 above membrane 62 and below the sealed lip of vase-shaped member 58. But once air or gas is vented to this point, compressing the lower chamber may create a high pressure against the filter and the membrane.

There may be several passageways and filters (filter means) such as the passageway 60 and filter 58 visible in FIG. 2, arranged radially about the dividing member 56, only one passageway and one filter being fully shown for convenience, a second being indicated at 58a. Alternatively and preferably a single filter 58 may be wrapped substantially as a cylinder and sealed at a continuous rib 56b of the otherwise vase-shaped member 56 connecting its upper and lower portions. We may concentrate attention on the lowest hydrophilic filter 58, or portion thereof, and the highest hydrophobic membrane 62, or portion thereof. The lower chamber 54 at its lower end terminates in a necked down portion 64 of the outer walls 50, forming an exit port 65. At its upper end the chamber 52 terminates in an open portion 66 of the walls 50 within which is fitted in substantially liquid tight fashion a fitting 68 comprising a spear or spike portion 70. The fitting 68 includes a passageway 72, communicating through the spear with the upper chamber 52, and terminates at its lower end in a centrally located nipple 68a.

Assume that the arrangement of filter unit 49 of FIG. 2 is substituted for the filter unit 10 with spear or spike 70 inserted to replace the spear or spike in container 28, and the necked down portion 64 to replace exit port 16. Operation may be initiated by first closing clamp 35. Next insert the spike into the seal of bottle or container 28. Then once or more squeeze lightly the upper chamber 52 above the lip of vase-shaped member 56 and relax to initiate liquid flow to establish a liquid level above the filters. Next lightly squeeze the lower chamber walls to expel air through hydrophobic membrane 62 and relax to insure liquid contact and flow of liquid through the hydrophilic filter 58, desirably sufficiently often to insure liquid contact with the entire area of the filter 58 and filling the lower chamber with liquid until liquid contacts hydrophobic membrane 62 from below, thereby preventing entrapment of air in the liquid path during administration. If necessary again squeeze and relax the walls of the upper chamber 52 to re-establish the upper liquid level. If the upper chamber liquid level is too high, the drip into the upper chamber 52 in its function as a drip chamber cannot be observed; if too low the hydrophilic filter 58 may not be completely covered and it is desirably so covered. Thereafter open the downstream clamp 35 and allow liquid to expel any air in the tubing 34, desirably for surety permitting some excess of liquid to flow into any suitable container. Once the air is completely expelled from tubing 34, attach the needle and make the venipuncture in the usual manner, to permit fluid flow to the patient. As liquid flows to the patient, replenishing liquid will flow through passageway 72 to nipple 68a and drip into the upper chamber 52.

Normally, the forward pressure on the filter 58 does not exceed the headpressure of the supply bottle or container 28, which normally has a cushion of compressible air or may be collapsible and expands as required, and therefore no support of the hydrophilic filter 58 on its downstream side may be necessary. Nevertheless when squeezing the lower chamber 54, a high back pressure may result, especially if all gas or air has been vented to the level of the hydrophobic membrane. In this event, if a clamp is applied to the tubing downstream, there is no way in which relief for the pressure resultant on the filter and membrane is afforded. Therefore upstream support for both the filter and membrane are desirable.

When the liquid from the supply container 28 is exhausted the liquid will continue to flow through the upper flexible tubing 32 and through the upper chamber 52, as though through a drip chamber. Air is prevented from passing into the lower chamber 54 by means of the wet hydrophilic filter 58 and the liquid reservoir 69 inside the vase-shaped member 56 between the lower part of hydrophilic filter 60 and the hydrophobic membrane 62. Although if the unit illustrated in FIG. 2 is tilted, for example by turning the upper portion clockwise, liquid may reach and pass in the reverse direction through the hydrophilic filter 58, the air or gas cannot flow in the forward direction to endanger the patient by air or gas entering the lower chamber 54.

In the event of a reverse differential pressure between the chambers, reverse liquid flow is prevented or blocked by the air or gas reservoir or trap 67 outside and around the vase-like member 58 and between its sealed rim and the lower, hydrophobic membrane 62.

Figure 3:
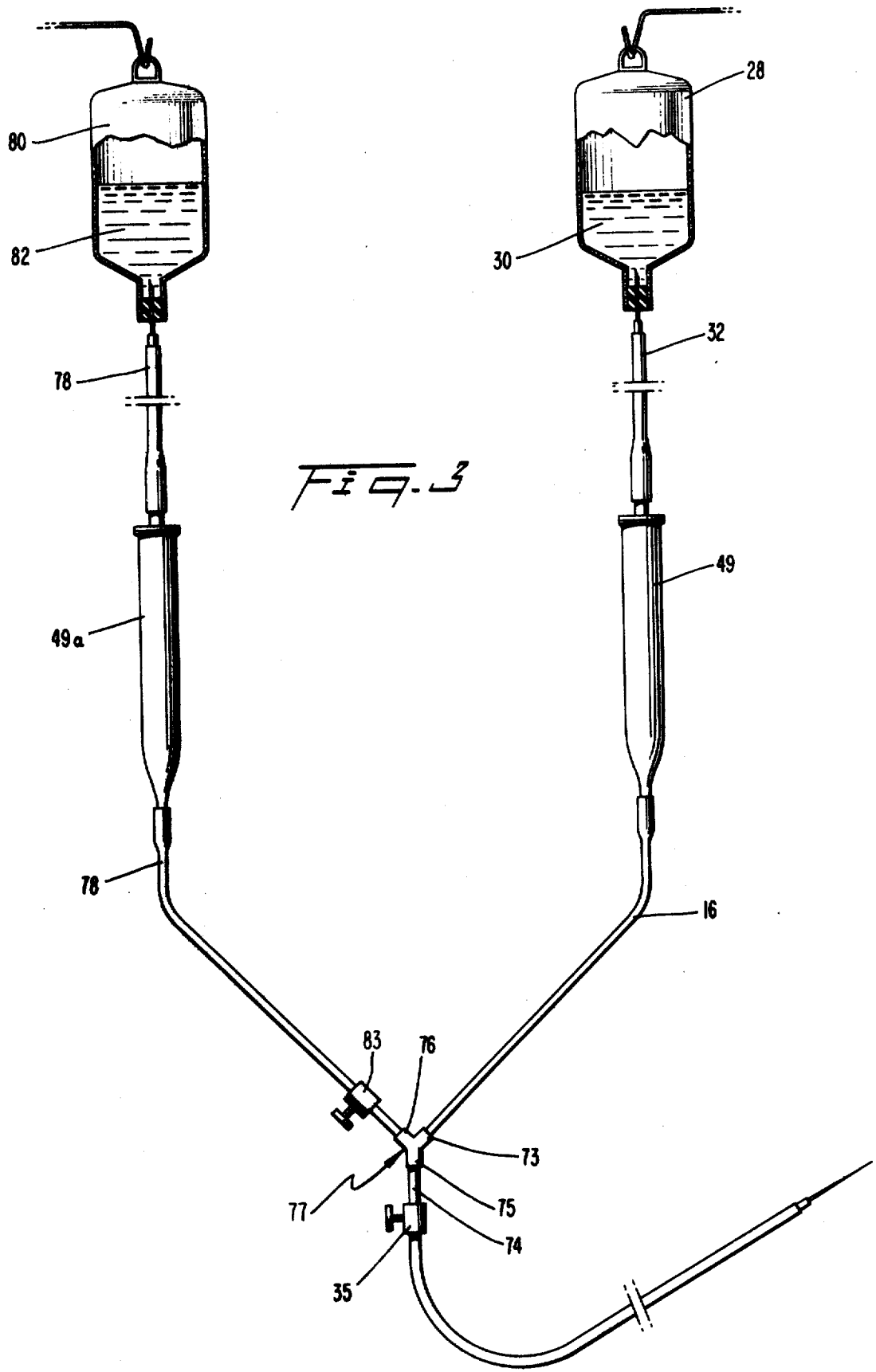
FIG. 3 is a partially schematic view showing the manner in which the embodiment of FIG. 2 may be employed in a so-called "piggyback" arrangement.

In FIG. 3 there is illustrated an arrangement like that of FIG. 1 using the filter unit 49 of FIG. 2 except that the lower flexible tubing 16 includes a Y connection 77. One upper branch 73 of the Y connection 77 leads to the flexible tubing 16, and the lower part of leg 75 of Y connection 77 is connected to flexible tubing 74 with a clamp 35 and leading to the patient. The other arm or branch 76 of the Y 77 is connected to a further flexible tubing 78 which leads to a second container 80. The container 80 contains a preferential or auxiliary solution 82 which is to be supplied to the patient, and is hung higher than container 28. The tubing 78 may if desired be continuous from the arm 76 of Y 77 to the auxiliary container 80. Nevertheless for reasons to be explained hereinafter preferably there is interposed, as illustrated in FIG. 3, a second unit 49a. The unit 49a may be like the unit 49, and connected between the reaches of tubing 78 from the container 80 and to the arm 76 of the Y 77, just as the unit 49 is connected between the reach of tubing 32 from container 28 and the reach of tubing 16 to the arm 73 of Y 77.

Operation in the absence of the second unit 49a, or with the clamp 83 closed, will be clear from the operation described in connection with the arrangement of FIG. 1. To initiate operation in the arrangement of FIG. 3 close clamps 35 and 83. Insert the spike into the rubber or rubber-like stopper of container 80. Lightly squeeze and relax the upper chamber of unit 49 to initiate liquid flow and establish a liquid level above the filters. Then squeeze and relax the lower chamber as required to fill the lower chamber with liquid until liquid contacts the hydrophobic membrane from below. Then open clamp 83 to fill the tubing 78 with liquid, and after closing clamp 83, open clamp 35 to expel all air or gas throughout the lower chamber and tubing 74 to the cannula. As understood the initiation of operation must guard against air or gas reaching or threatening to reach the cannula and the patient. Once initiated the operation will be like that described in connection with FIG. 1. Note that the liquid collects and drips at the nipple 68a (FIG. 2) of unit 49 as it flows. Therefore if the walls or a portion thereof of the upper chamber 52 of unit 49 in FIG. 3 are transparent to allow view of the drip, an observer can judge the flow of solution in the usual manner.

If it is desired to start flow of the secondary solution 82, a spike may be entered into the stopper of container 80, and (assuming the absence of the second unit 49a) making sure that all air has left tubing 78 to the clamp 83, this clamp may be opened.

Because the second or auxiliary container 80 is at a higher level than the container 28, the flow from the auxiliary solution 82, assuming approximately equal densities for the solutions, will tend to displace the flow from the solution 30 in the primary container 28. As soon as the level of the auxiliary supply reaches the level of the primary supply of liquid, both will flow.

It may occur that the primary solution 30 may become exhausted, in which event, as explained hereinbefore, flow of liquid 30 continues in tubing 32 only so far as the unit 49. Although the flow of liquid 30 there ceases, the flow in the tubing 78, if tubing 78 is continuous, continues and may lead to air entering the Y connection 77. The pressure at the junction may cause a flow of liquid to proceed down the leg 75 of Y 77 and eventually cause the introduction of air into the lower flexible tubing 74. To prevent this possibility, the unit 49a is inserted in the tubing 78 as described above. With unit 49a in the line, flow of liquid 82 from auxiliary container 80 is stopped when the liquid level reaches the unit 49a, as will be understood from the foregoing. Similarly flow of liquid 30 from primary container 28 stops at unit 49. In no case can air or gas enter below these units and reach the tubing 74 leading to the patient.

An embodiment of a unit 123 corresponding to that illustrated in FIG. 4 may be constructed in the following manner. A Cutter's standard vented bottle spike 70' may be used in lieu of spike 70 of FIG. 2. A filter support or core 57 has a cylindrical body 57a and a coaxial cylindrical lip 57b. Lands 57c and grooves 57d extend circumferentially about the outer part of cylindrical body 57a, except for an axially extending rib or spine 57e which runs the length of the body 57a. Adjacent lip 57b is a shoulder 57f, and a smaller diameter rim 57g. At the opposite axial end of body 57a is another, lower rim 57h of like diameter to the first rim 57g. The alternate circumferential lands 57c, of like diameters to the rims 57g and 57h, and grooves 57d extend about the body, except at the axially extending rib or spine 57e. Diametrically opposite the rib 57e a through, axial slot 57p extends from the upper rim 57g about one-third the axial length of the body 57a, and in line therewith an axial groove 57n of a radial length from the axis of the body 57a less than the lands and continues to the second rim 57h.

About the core or filter support 57 is rolled a rectangular hydrophilic filter 124 having the desired pore fineness, by way of example, a 0.2 micrometer filter, so that two opposite edges envelop the rims 57g and 57h and the other two edges lie on th spine 57e. From a fluid mechanics standpoint the filter pores need only be of a fineness to insure that when wet the bubble point will be sufficiently great to withstand any expected pressure across the filter, i.e. microporous. Nevertheless a finer pore size is usually useful for filtering reasons. The filter pore size of 0.2 micrometers was selected to filter bacteria from the filtrate passing toward the patient. The edges of the filter 124 are heat sealed to the rims and spine. The core 57 is substantially a standard filter support core.

A rigid sleeve 126 has an internal diameter equal to that of the shoulder 57f and an external diameter substantially equal to that of the lip 57b, one end of the sleeve 126 being plain. The sleeve tube 126 is slipped at its one plain, upper end over the shoulder 57f and against the lip 57b and sealed thereto coaxially with the core 57 by any suitable means, as by heat sealing or by solvent bonding. At the other, lower axial end the sleeve 126 has a flanged portion 128.

A resilient, frustroconical tubular section 130 at its larger end is flanged and engaged and sealed to the flanged portion 128 and terminates at its other axial end in a smaller diameter fitting 132 for a standard flexible tubing 133, so that the tubing may be slipped over the fitting 132 and will be held in frictional, liquid and air tight engagement. It may be further sealed if desired.

A cylindrical resilient, transparent tubular member 134 has an internal diameter substantially equal to the external diameter of the sleeve 126 and lip 57b. One end of this tubular member is slipped over the lip 57b and a portion of the non-flanged end of the sleeve 126, and sealed to these parts by any suitable means such as solvent binding. The other end of the member 134 is now coupled to the flange 136 of the Cutter's vented bottle spike 70'. A rubber or rubber-like washer 137 may be used to seal the member 134 to the flange 136 of the bottle spike 70'. The bottle spike 70' comprises a spear or spike part 138 and an automatic valve portion 140 which admits air as required to replace liquid drained from a bottle such as container 28 into which the spike part 138 is inserted, but prohibits liquid flow in the reverse direction. A filter 139 filters the incoming air. The bottle spike also includes a drip nipple 142 with which apertures 144 in the spike portion or spear 138 communicate through an internal conduit so that the liquid may drip, in the usual fashion, from the nipple 142.

A membrane support 150 comprises an annular rim 152 from which coaxially extends an annular lip 154 having an external diameter substantially equal to the internal diameter of the filter core 57, forming a shoulder 156. The lip 154 is fit inside the lower end of core 57 and sealed by any suitable means, as by solvent bonding, to the end of the body 57a remote from the lip 57b, with the shoulder 156 bearing against the lower end of the cylindrical body 57a. A pair of inner cross members 158 at the axial end 153 of the rim 152 remote from the lip 154 flush with the axial edge of that end, are provided. A hydrophobic membrane 160, which may also have a pore size of 0.2 micrometers, circular in shape with a diameter substantially equal to the outer diameter of the rim 152 is sealed to this same end 153 by any suitable means, as by heat sealing, and preferably also to the cross members 158, to afford upstream membrane support.

It is now apparent that when assembled as described above, the arrangement of FIG. 4 provides a filter unit 123 having an upper chamber 168 defined in part by the resilient member 134, and a lower chamber 170 defined in part by the resilient frustroconical tubular section 130. The upper filter 124 and lower membrane 160 separate the two chambers 168 and 170.

In operation, the spike is spiked into a desired solution container in the usual manner. The fitting 132 is attached to the flexible tubing reaching to the needle to be inserted into the patient's vein, and having a clamp. The steps now followed are those similar to the steps described in connection with initiation of operation in connection with the unit of FIG. 2, and will be understood by those skilled in the art without further description. If desired units such as unit 162 may be used in the manner described for the unit 49 of FIG. 3.

Note, nevertheless, that the rigid sleeve 126 serves to protect the fragile filter 124, from physical damage. The upper chamber 168 defined in part by the resilient cylindrical tubular member 134 also acts as a drip chamber, for the liquid will drip in customary fashion from the nipple 142 into the upper chamber 168. The member 134 may be of transparent plasticized polyvinyl chloride, as may also be the frustroconical tubular section 130. Thus these respective walls of the upper and lower chamber may be squeezed or flexed and operate as a pump as described to initiate operation. The drip into the upper chamber may be viewed through the resilient tubular member 134 to monitor liquid flow as in the usual manner with drip chambers. The unit 123 may be used in the same manner as described for the unit 10 or the unit 49.

If desired some of the components described above as separate elements sealed together may be molded as a single monolithic element. It is also apparent that the units of the invention may be constructed of inexpensive materials in an economical fashion, to perform the functions described. By a microporous filter or membrane I mean one having a pore size between about 25 nanometers and about 25 micrometers.

From the foregoing it will be apparent the novel filter unit of the invention has several advantages.

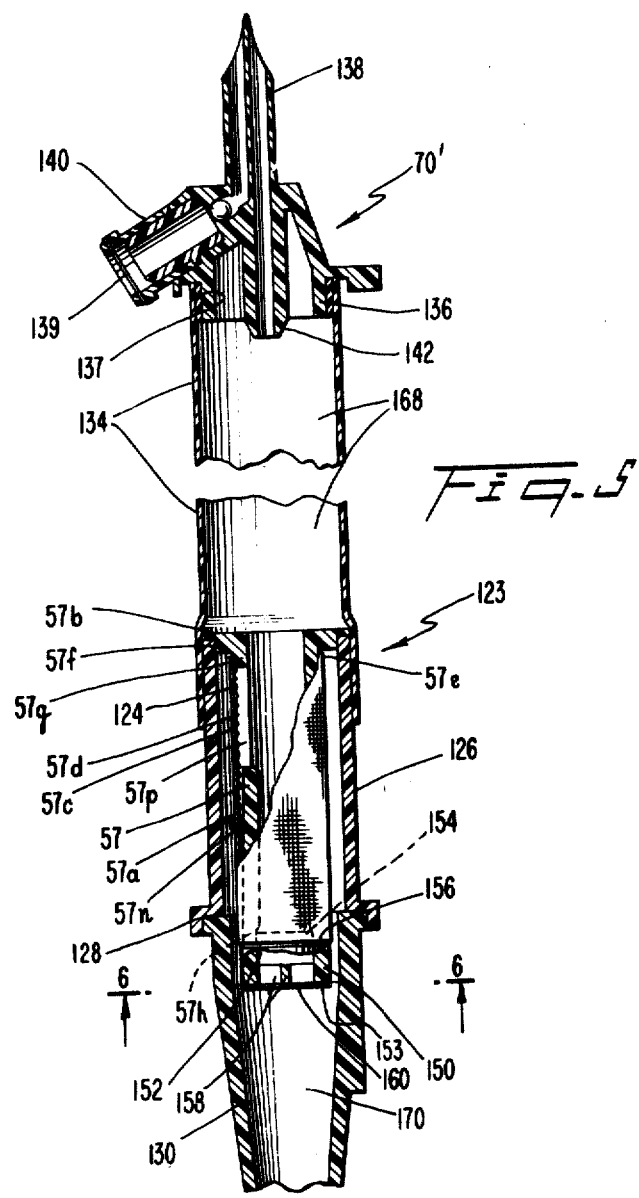

What is claimed is:

1. A filter unit designed to have, when in operation, a vertical axis,
    said unit having an upper chamber and a lower chamber along said axis,
    a hydrophilic filter separating said chambers,
    a hydrophobic membrane separating said chambers and in operation lower along said axis than said hydrophilic filter,
    a gas reservoir in the lower chamber above the membrane and below the filter, and
    a liquid reservoir in the upper chamber above the membrane and below the filter,
    whereby in operation liquid is trapped in the liquid reservoir and gas is trapped in the gas reservoir.

2. A filter unit having:
    a liquid inlet chamber and a liquid outlet chamber,
    a hydrophobic filter means,
    hydrophilic filter means,
    said chambers being separated by said hydrophilic filter means and being separated by said hydrophobic filter means,
    a liquid reservoir in said inlet chamber between said filter means, and
    a gas reservoir in said outlet chamber between said filter means,
    said holder having a normal orientation in use in which said hydrophilic filter means lie entirely at an elevation above that of said hydrophobic filter means,
    whereby in the presence of liquid flow in said inlet chamber during forward differential pressure liquid flows through said hydrophilic filter means from said inlet chamber to said outlet chamber,
    whereby in the presence of liquid flow in the inlet chamber, gas below said hydrophobic filter in said outlet chamber is relieved to said inlet chamber through said hydrophobic filter means,
    whereby if liquid supply to said inlet chamber fails and a forward pressure differential exists between said chambers, forward gas flow is prevented by the wetted hydrophilic filter means and liquid trapped in said liquid reservoir above the hydrophobic filter, and
    whereby if a reverse pressure differential exists reverse liquid flow is prevented by the hydrophobic filter means and gas trapped in said gas reservoir below the hydrophilic filter means.

3. A filter unit as claimed in claim 2, said inlet chamber having a resilient outer wall.

4. A filter unit as claimed in claim 2, said outlet chamber having a resilient outer wall.

5. A filter unit as claimed in claim 2, said unit further comprising outer walls which surround said chambers, and a rigid member sealed to said walls and to which said filter means are sealed.

6. A filter and a filter unit as claimed in claim 2, said hydrophilic filter mean having a filter support on the upstream side of the filter.

7. A filter unit having an entrance and an exit,
    said unit having a first chamber to receive liquid from and communicating with said entrance, and a second chamber to supply liquid to and communicating with said exit,
    a first passageway for liquid from said first to said second chamber,
    a microporous hydrophilic filter in said first passageway to filter liquid flowing through said first passageway,
    a second passageway for gas to flow from said second chamber to said first chamber,
    a microporous hydrophobic membrane in said second passageway to admit gas to flow from said second to said first chamber,
    in the normal orientation of said holder during operation, said hydrophilic filter being at a higher elevation than that of said hydrophobic membrane,
    a liquid reservoir between said filter and said membrane as part of said first chamber, and
    a gas reservoir between said filter and said membrane as part of said second chamber,
    whereby, in operation:
    liquid flow from entrance to exit is filtered by said hydrophilic filter,
    gas in said second chamber is vented to said first chamber through said hydrophobic membrane, except for gas trapped in said gas reservoir between the elevations of said filters,
    in the event of the absence of liquid at the entrance the flow of gas from said first to said second chamber is blocked by the wetted hydrophilic filter and liquid trapped in said liquid reservoir against said hydrophobic membrane,
    in the event of reverse pressure differential between the chambers, reverse liquid flow is blocked by the hydrophobic membrane and the gas trapped in said gas reservoir against the hydrophilic filter, and
    gas below the hydrophobic membrane is vented from the second to the first chamber.

8. A filter unit having a liquid inlet chamber and a liquid outlet chamber,
    a hydrophilic filter means mounted between said chambers to filter any liquid flow from said inlet chamber to said outlet chamber,
    a hydrophobic membrane means mounted between said chambers to vent and pass excess gas from said outlet chamber to said inlet chamber,
    in the normal orientation of said holder during operation, said hydrophilic filter means being at a higher elevation than that of said hydrophobic membrane means,
    a liquid reservoir in said inlet chamber above said hydrophobic membrane means, and
    a gas reservoir in said outlet chamber below said hydrophilic filter means.

9. A filter unit as claimed in claim 8,
    said outlet chamber including a rigid wall portion about the said filter thereby to protect the filter.

10. A filter unit as claimed in claim 8, said inlet chamber having a liquid supply inlet in the form of a nipple and comprising a transparent wall portion, whereby said upper chamber also may serve as a drip chamber.

11. A filter unit as claimed in claim 8, said inlet chamber having a resilient, transparent wall and a rigid wall, said rigid wall surrounding and spaced from said filter thereby to protect the filter.

12. A filter unit as claimed in claim 8, said unit comprising a cylindrical filter support member having lands and grooves, said filter means comprising a filter rolled on and supported by said lands, a rigid cylindrical sleeve member coaxially surrounding said filter support and filter and sealed to said support member at the support member's upper end, a frustroconical resilient tubular member coaxially sealed to said rigid sleeve member thereby to form said lower chamber, a resilient cylindrical member sealed to said rigid sleeve member at the rigid sleeve member's seal to said filter support, thereby providing resilient walls for said inlet chamber.

13. A filter unit as claimed in claim 12, further comprising a further member sealed to the end of said resilient cylindrical member remote from the seal of said resilient cylindrical member to said rigid sleeve member, said further member comprising a nipple for liquid drip as part of the inlet for said inlet chamber.

14. A filter unit having, when in use a vertical axis, and comprising:
   a pair of chambers in said holder, one at an elevation along said axis greater than that of the other,
   at least one hydrophilic filter separating said chambers,
   at least one hydrophobic membrane separating said chambers,
   the lowest said hydrophilic filter being at an elevation along said axis higher than that of the highest hydrophobic membrane,
   a liquid reservoir in said greater elevation chamber above said hydrophobic membrane, and
   a gas reservoir in the lower elevation chamber below said hydrophilic filter.

15. A filter unit as claimed in claim 14, the greater elevation chamber having resilient walls.

16. A filter unit as claimed in claim 14, the lower elevation chamber having resilient walls.

17. A filter unit as claimed in claim 14, each of said chambers having resilient walls.

18. A filter unit as claimed in claim 17, said hydrophilic filter having a filter support in the up-stream direction.

19. The combination comprising:
   (a) a filter unit having:
      a liquid inlet chamber and a liquid outlet chamber,
      hydrophilic filter means mounted between said chambers to filter any liquid flow from said inlet chamber to said outlet chamber,
      a hydrophobic membrane means mounted between said chambers to vent and pass excess gas from said outlet chamber to said inlet chamber,
      in the normal orientation of said holder during operation, said hydrophilic filter means being at a higher elevation than that of said hydrophobic membrane means,
      a liquid reservoir in said inlet chamber above said hydrophobic membrane means, and
      a gas reservoir in said outlet chamber below said hydrophilic filter means,
   (b) a liquid passageway having an inlet connected to receive liquid from said outlet chamber and an outlet, and
   (c) a branch liquid passageway having an outlet connected to said first-mentioned passageway and having an inlet for connection to receive an auxiliary liquid supply.

20. The combination claimed in claim 18, further comprising:
   (d) a second filter unit having an inlet and an outlet, said second unit outlet being connected to said branch passageway inlet.

21. The combination claimed in claim 19, further comprising:
   (d) a second filter unit having:
      a liquid inlet chamber and a liquid outlet chamber,
      a second hydrophilic filter means mounted between said second unit chambers to filter any liquid flow from said second unit inlet chamber to said second unit outlet chamber,
      a second hydrophobic membrane means mounted between said second unit chambers to vent and pass excess gas from said second unit outlet chamber to said second unit inlet chamber,
      in the normal orientation of said second unit during operation, said second hydrophilic filter means being at a higher elevation than that of said second hydrophobic membrane means,
      a second liquid reservoir in said second unit inlet chamber above said second unit hydrophobic membrane means, and
      a second gas reservoir in said second unit outlet chamber below said second unit hydrophobic filter means,
      said second unit outlet chamber being connected to said branch passageway inlet.

* * * * *

UNITED STATES PATENT OFFICE
CERTIFICATE OF CORRECTION

Patent No. 4,116,646            Dated September 26, 1978

Inventor(s) James H. Edwards

It is certified that error appears in the above-identified patent and that said Letters Patent are hereby corrected as shown below:

Figures 2, 3 and 5 of the drawings should appear as shown on the attached sheets.

*Signed and Sealed this*

*Twenty-seventh* Day of *February 1979*

[SEAL]

Attest:

RUTH C. MASON
*Attesting Officer*

DONALD W. BANNER
*Commissioner of Patents and Trademarks*